US008822416B2

(12) United States Patent
Sheil et al.

(10) Patent No.: US 8,822,416 B2
(45) Date of Patent: Sep. 2, 2014

(54) TOPICAL ANALGESIC COMPOSITION

(75) Inventors: Meredith Sheil, Hunters Hill (AU);
Allan Giffard, Yarra Glen (AU);
Charles Robert Olsson, Gordon (AU)

(73) Assignee: Animal Ethics Pty Ltd. (AU)

( * ) Notice: Subject to any disclaimer, the term of this patent is extended or adjusted under 35 U.S.C. 154(b) by 1626 days.

(21) Appl. No.: 11/856,190

(22) Filed: Sep. 17, 2007

(65) Prior Publication Data

US 2008/0131527 A1    Jun. 5, 2008

Related U.S. Application Data

(62) Division of application No. PCT/AU2006/000337, filed on Mar. 15, 2006.

(30) Foreign Application Priority Data

Mar. 15, 2005  (AU) ................................ 2005901250
May 6, 2005    (AU) ................................ 2005902296
Sep. 14, 2005  (AU) ................................ 2005905062
Dec. 12, 2005  (AU) ................................ 2005906965

(51) Int. Cl.
*A61K 38/00*        (2006.01)

(52) U.S. Cl.
USPC ............................ 514/9.4; 514/330; 514/817

(58) Field of Classification Search
None
See application file for complete search history.

(56) References Cited

U.S. PATENT DOCUMENTS

| 3,832,460 | A | 8/1974 | Kosti |
| 4,248,855 | A | 2/1981 | Blank et al. |
| 5,098,417 | A | 3/1992 | Yamazaki et al. |
| 5,563,153 | A | 10/1996 | Mueller et al. |
| 5,585,398 | A | 12/1996 | Ernst |
| 5,804,213 | A | 9/1998 | Rolf et al. |
| 5,827,529 | A | 10/1998 | Ono et al. |
| 5,942,543 | A | 8/1999 | Ernst |
| 6,075,059 | A | 6/2000 | Reader |
| 6,146,654 | A | 11/2000 | Kubo |
| 6,159,498 | A | 12/2000 | Tapolsky et al. |
| 6,295,469 | B1 * | 9/2001 | Linkwitz et al. ............... 604/20 |
| 6,375,963 | B1 | 4/2002 | Repka et al. |
| 6,562,363 | B1 * | 5/2003 | Mantelle et al. ............. 424/434 |
| 6,620,852 | B2 | 9/2003 | Brogan et al. |
| 2002/0006435 | A1 * | 1/2002 | Samuels et al. ............. 424/449 |
| 2003/0059379 | A1 | 3/2003 | Andersen et al. |
| 2003/0185873 | A1 | 10/2003 | Chasin et al. |
| 2003/0232091 | A1 | 12/2003 | Shefer et al. |
| 2004/0086575 | A1 * | 5/2004 | Smith .......................... 424/643 |
| 2005/0256187 | A1 | 11/2005 | Liedtke |

FOREIGN PATENT DOCUMENTS

| AU | 524658 | 11/1978 |
| AU | 647784 | 3/1991 |
| EP | 0040862 | 2/1981 |
| EP | 1550441 | 6/2005 |
| GB | 2198642 | 6/1988 |
| GB | 2288734 | 1/1995 |
| JP | 07157427 | 12/1993 |
| WO | WO 93/19739 | 10/1993 |
| WO | WO 96/10389 | 4/1996 |
| WO | WO 98/39042 | 9/1998 |
| WO | WO 99/55287 | 11/1999 |
| WO | WO 00/30630 | 6/2000 |
| WO | WO 00/71089 | 11/2000 |
| WO | WO-01/22907 A1 | 4/2001 |
| WO | WO 01/30287 | 5/2001 |
| WO | WO 01/37890 | 5/2001 |
| WO | WO 01/50994 | 7/2001 |
| WO | WO 01/54679 | 8/2001 |
| WO | WO 2004/058329 | 7/2004 |
| WO | WO 2005/032521 | 4/2005 |

OTHER PUBLICATIONS

Fluidic, [online], Meriam-Webster online dictionary, Retrieved [Mar. 7, 2011], Retrieved from URL:<http://www.merriam-webster.com/dictionary/fluidic>.*
Sutherland et al., Effect of local anaesthetic combined with wound cauterisation on the cortisol response to dehorning calves, Aus Vet. J., Mar. 2002; 80(3); 165-167.
Levot et al., Evaluation of dressings to aid healing of mulesing wounds on sheep, Aust Vet J., Nov. 1989; 66(11) 358-361.
Pearse et al., Comparison of a liquid and a powder insecticidal dresssing to aid healing and prevent flystrike of mulesing would in lambs, Aust Vet J. May 1991; 68(5): 163-164.
Lubrizol, Neutralizing carbopol and pemulen polymers in aqueous and hydroalcoholic systems, Technical Data Sheet, TDS-237, Jan. 2002:1-3.
Bren, Helping wounds heal, U.S. Food and Drug Administration, May-Jun. 2002: 1-8.
Tuckley, The pharmacology of local anaesthetic agents, Pharmocology, Issue 4 (1994), Article 7.
Chapman, Progress towards a non-surgical alternative to the mules operation for the control of blowfly strike, ISSN 0043-7875/93. Wool Tech. Sheep Breed., 1993, 41:1-10.
Farquharson et al., Historic and current non-surgical alternatives to . . . , Proceedings of the Australian Sheep Veterinarians 2005—Gold Coast Conference, vol. 15, pp. 157-161.

(Continued)

*Primary Examiner* — Lezah Roberts
*Assistant Examiner* — Nannette Holloman
(74) *Attorney, Agent, or Firm* — Stefan J. Kirchanski; Venable LLP (57) ABSTRACT

This invention concerns a synergistic combination of a topical anesthetic and wound barrier forming agent capable of providing extended analgesia of 'significant open wounds' (that being, for example, a laceration, surgical incision, abrasion, ulcer or burn, but not being a minor cut, scratch, sting, burn or abrasion) in which conventional management alternatives (such as suturing and/or administration of injected or systemic analgesia) are impractical, unaffordable or otherwise unavailable.

9 Claims, 2 Drawing Sheets

(56) References Cited

OTHER PUBLICATIONS

Ilkiw, Local anesthesia and local anesthetic techniques, World Small Animal Veterinary Association Worl Congress—Vancouver 2001:1-5.

Glattes, Rudolph C et al, "A simple, accurate method to conform placement of intra-articular knew injection," American Journal of Sports Medicine, American Ortopaedic Society for Sports Medicine, vol. 32, No. 4, Jun. 1, 2004, pp. 1029-1031.

* cited by examiner

TOPICAL ANALGESIC COMPOSITION

CROSS-REFERENCE TO PRIOR APPLICATIONS

This application is a continuation-in-part of international application PCT/AU2006/000337 filed Mar. 15, 2006 which designated the U.S and additionally claims priority from Australian provisional patent application 2005901250 filed Mar. 15, 2005, Australian provisional patent application 2005902296 filed May 6, 2005, Australian provisional patent application 2005905062 filed Sep. 14, 2005, and Australian provisional patent application 2005906965 filed Dec. 12, 2005, the content of which provisional applications is included herein by reference.

U.S. GOVERNMENT SUPPORT

Not Applicable

BACKGROUND OF THE INVENTION

1. Technical Field

This invention relates to a topical analgesic composition; in particular, the invention concerns a synergistic combination of a topical anesthetic and wound barrier forming agent capable of providing extended analgesia of 'significant open wounds'—that being, for example, a laceration, surgical incision, abrasion, ulcer or burn, but not being a minor cut, scratch, sting, burn or abrasion.

2. Description of the Background Art

Pain from an open wound (e.g. laceration, surgical incision, ulcer or burn) is initiated by a stimulation of traumatized nerve fibers and is intensified by a local inflammatory response that occurs over ensuing 24-48 hours and results in local tissue swelling and edema. Pain from an open wound is also further intensified and prolonged by a sensitization reaction of higher nerve function which also occurs over ensuing hours and days, and may lead to lower pain thresholds and prolonged hypersensitivity of surrounding tissues. Such wounds are usually treated by closing or sealing the wound, such as by suturing, adhesive plastering, bandaging or other practice. Closing the wound stops bleeding, protects traumatized tissues and nerve fibers from dehydration, ongoing environmental exposure, risk of infection and ongoing painful stimulation. Pain therefore abates as the inflammatory response and tissue edema subsides.

Where available, pain related to such wounds is managed using systemic analgesia (such as oral, IM or IV opioids or non-steroidal anti-inflammatory agents) and/or injected local anesthetic agents. In this situation, injected local anesthetic agents are generally used for short term wound anesthesia prior to debriding, suturing or otherwise closing or treating the wound. They may also be indicated as providing prolonged pain relief during and following surgical procedures in which the wound is generally closed. Local anesthetic agents generally act by blocking nerve conduction, thereby reducing or eliminating pain sensation for the duration of their action, which is generally in the order of 30 minutes to several hours depending on the agent and method of administration. Prolonged analgesia may be achieved using injections of anesthetic agents having a long duration of action, such as bupivacaine (duration of action 6-8 hours following injection), or by using repeated or continuous subcutaneous injection or infusion, or by combining an anesthetic agent with a special implantable or injectable delivery vehicle that results in slow-release diffusion (US Patent Application No. 2003/0185873 A1).

Some local anesthetic agents may be applied topically; however, they have reduced efficacy and potency when used with this method of application. They typically only provide anesthesia for 30 to 60 minutes in open wound situations. This may be adequate to anaesthetize the wound in preparation for debriding, cleaning, suturing etc; however, they are rarely indicated for analgesia of acute and significant open wounds other than for this short term application. Slow-release vehicles may prolong the duration of topical anesthesia to a certain extent, but not usually greater than a doubling of the 30 minute to 60 minute analgesic period.

In many cases, however, the management strategies for closing acute and significant open wounds are impractical, unaffordable or unavailable and wounds are therefore left open to heal by secondary intention. This applies to a very large number of acute traumatic and/or surgically induced wounds, particularly in animals. Examples include:

1. Wounds in animals, including traumatic wounds and/or those caused by husbandry procedures such as branding, castration, dehorning, tail docking and mulesing.
2. Wounds in mass human trauma situations, such as earthquakes, floods and wars.
3. Wounds that occur in remote locations and Third World countries where medical attention may be limited or unavailable.

Where an acute and significant laceration and/or traumatic wound remains open and/or otherwise untreated for a prolonged period, bleeding continues unless or until natural clotting occurs. In addition, ongoing exposure of traumatized tissues results in increased risk of contamination and/or infection as well as ongoing painful stimulation of traumatized nerve fibers. This may be exacerbated by the local and systemic inflammatory and immune responses that occur when tissue and blood components are exposed to foreign (external) materials or surfaces. Inflammatory exudates contain many factors that cause and/or exacerbate pain. In this situation, pain may eventually abate as a natural 'covering' or 'seal' forms over the wound due to clotting and crusting of blood and inflammatory exudates. This serves to protect raw nerve endings from exposure to the environment. However, pain may continue or intensify during the healing process if such a seal dries out and/or becomes infected and cracks open or becomes ulcerated, thereby leaving raw nerve tissue exposed to the environment again.

Burn injuries constitute a prominent example of a significant open wound that cannot be closed by suturing. Where pain from burn injury is significant it is usually managed with systemic analgesia, however burns are typically also 'sealed', 'covered' or 'closed' by the application of 'barrier' formulations (which usually consisting of thick oil or cream based topical applications) and/or bandaging, or by the application of films, artificial 'skins' or skin grafts. Such 'barrier preparations' act to provide an immediate cover over the wound, which prevents heat and water loss from the wound surface, and act as a barrier against bacterial contamination, thus aiding the healing process and reducing morbidity. They are also known to provide a measure of analgesia. (Bose B. Burn. Wound Dressing with Human Amniotic Membrane. Annals of the Royal College of Surgeons of England. 61(6):444-7, 1979 Nov. 2, Weiss R A. Goldman M P Interpenetrating Polymer Network Wound Dressing Versus Petrolatum Following Facial CO2 Laser Resurfacing: A Bilateral Comparison. Dermatologic Surgery. 27(5):449-51, 2001 May). However, they are not potent at providing wound anesthesia in the acute situation (in which nerve endings are stimulated and instigate pain sensitization and wound hyperalgesia in response to being cut, burned or traumatized), but rather they act to reduce pain in the later stages by placing a moist and constant seal over exposed nerve endings. This protects against drying and ongoing stimulation by interaction with the open environment while wounds re-epithelialize and nerve fibers regenerate. Despite being well recognized for this particular open wound situation, barrier formulations are not generally indicated for other open wounds such as those due to trauma and lacerations. This is principally because: A) barrier formulations generally cannot adhere adequately to wounds that are actively bleeding; and/or B) alternative treatments such as suturing, adhesive bandaging or otherwise closing the wound are available or preferred.

Significant cuts, abrasions and lacerations that remain open and/or bleeding due to impracticality, lack of availability or affordability of preferred management strategies (such as primary closure and/or systemic analgesia) at present therefore receive little to no treatment—either via analgesic administration or wound barrier application.

It is the present inventors' novel contention that topical anesthetic agents can be used effectively to manage and reduce pain in these situations if combined with carriers having the following characteristics: 1) that they promote and/or prolong anesthetic absorption into an open wound; and 2) that they provide a long-lasting barrier (seal) over the open wound. It is the present inventors' contention that the early anesthetic effects of topical anesthetic agents can work synergistically with analgesic effects of barrier formulations to provide extended wound analgesia for all such indications.

It is important to note that until now analgesia from wound pain has not even been considered in most of these situations. Where it has been considered, topical anesthesia has been considered too slow acting, of too short a duration and/or of ineffective potency to provide a suitably effective sole mechanism of analgesia for this indication. Similarly, had it previously been considered, barrier treatments would not have been felt to be practical or effective at providing significant analgesia in such situations due to their inability to adhere to actively bleeding/weeping wounds, or the potential to interfere with the absorption of anesthetic agents. Nevertheless, the present inventors had the novel idea that synergistic interaction between the early anesthetic effects of topical anesthesia and the later analgesic effects of wound barrier formulations had the potential to be harnessed to provide a mechanism of effecting simple, effective and prolonged analgesia of significant wounds that were likely to remain open or otherwise untreated for prolonged periods. This novel combination is not taught by the prior art for at least the reasons given below.

Many/most of the known topical anesthetic compositions are designed for use on intact skin and therefore are not suitable for this indication. Examples include RESOLVE™, EMLA™ and AMETOPP™. These compositions are recommended for anesthesia of skin prior to minor procedures (such as performing needle insertion) or for temporary relief of minor skin irritations (such as minor cuts, stings and grazes). Because the skin acts as a barrier that prevents local anesthetic agents from reaching the subcutaneous nerve fibers on which they act, these compositions contain relatively high anesthetic concentrations compared with injectable compositions (to improve potency) and may contain promoters (skin penetration enhancers) to aid absorption through the skin. Despite this, they require prolonged (30-60 min) contact with the skin to achieve an anesthetic effect. This usually requires covering the anesthetic composition with gauze, wrap or other medical covering, or application of an impregnated patch to maintain prolonged contact. Repeat applications are required to maintain anesthesia longer than 30-60 minutes.

Because they are designed for intact skin, most do not contain vasoconstricting agents or agents for forming a wound barrier, which would be considered likely to reduce their potency and duration of effect when used on intact skin. However, several of these factors may combine to increase the risk of high level absorption if the agents are used on significant open wounds, for which they are therefore contra-indicated in many/most situations.

Many other known topical anesthetic formulations are specifically designed for use on mucous membranes, such as in the eyes or mouth. Topical anesthesia is more rapid and efficacious when used on such regions as the structure of skin allows easy penetration and anesthetic agents have more direct access to nerve fibers. Topical anesthetic compositions are therefore frequently used to provide pain relief for lesions and/or procedures in the eyes and mouth. Some commercially available compositions include XYLOCAINE VISCOUS™, and AAA™ mouth and throat spray. However, because of rapid penetration via mucous membranes, there is also a risk of rapid systemic absorption of the anesthetic agents away from the local tissues and into the blood stream. This has the capacity to reduce the duration of the anesthetic effect and to increase the risk of systemic toxicity. Because of this, such compositions usually contain relatively low anesthetic concentrations and/or are not formulated in carriers designed to achieve intrinsic analgesia of significant open wounds due to a barrier effect and are therefore also inappropriate for this indication.

Topical local anesthetic compositions have been trialled and/or recommended for use in small to medium lacerations immediately prior to suturing. Examples of liquid anesthetic compositions that have been trialled and/or recommended for use on small to medium lacerations include TAC (tetracaine, adrenaline and cocaine) and LET (lidocaine, epinephrine and tetracaine), being combinations of high dose anesthetic agents and vasoconstrictors. These compositions have been designed to provide short term anesthesia (usually 30 mins to 1 hour) and control bleeding, which allows the wounds to be cleaned and sutured, avoiding the need for local anesthetic infiltration. Such compositions can be as effective as injected lignocaine at anesthetizing a wound for suturing, particularly on the face and scalp (Stewart A M, Simpson P, Rosenberg N M. Use of topical lidocaine in pediatric laceration repair: A review of topical anesthetics. Ped Emerg Care. 1998; 14:419-423). These compositions contain higher doses of local anesthetic agents to improve potency and anesthetic effect. The risk of systemic absorption is reduced by including a vasoconstrictor, but also by limiting the use of the compositions to wounds below a certain size. Such compositions are generally applied by soaking a gauze in the composition and placing it on the wound, with repeated applications as required.

Sterile gels have been used as carriers for such indications. U.S. Pat. No. 5,563,153 is for an anesthetic composition having GELFOAM™ as a carrier, and U.S. Pat. No. 6,620,852 is for an anesthetic composition having SURGILUBE™ as a carrier. Such compositions, however, have not been designed to provide extended pain relief for wounds that are likely to remain open for prolonged periods and the duration of anesthetic effect on open wound situations is generally limited to ½ to 2 hours without repeat applications.

With regard to U.S. Pat. No. 5,563,153, the anesthetic composition having GELFOAM™ as a carrier is applied as a gelatinous paste (having the consistency of peanut butter) to an open wound and is principally designed to be used prior to repair or suturing the wound "Tackiness" is mentioned as being a desirable characteristic of the carrier; however, this is to prevent the actives running off the wound and into the eyes or mouth where they may exert increased toxicity. Easy removal by saline irrigation is also mentioned. This is so that the gel matrix can be removed once the wound is prepared for suturing. In Example 1 of U.S. Pat. No. 5,563,153, it is mentioned that the gel was applied to a wound and then covered by a gauze, suggesting a lack of intrinsic adhesion to the wound. Furthermore, it is mentioned that the gel appeared to "melt" when it entered the wound and was easily irrigated away. Hence, GELFOAM™ was not intended to provide a long-lasting barrier (seal) over the open wound, nor was it intended to provide a prolonged analgesic effect due to intrinsic characteristics of the gel.

With regard to U.S. Pat. No. 6,620,852, the anesthetic composition has SURGILUBE™ as a carrier and, being free-flowing, is typically applied to an open wound by way of dripping onto the wound or by soaking and covering with a gauze. Again SURGILUBE™ was intended for use on open wounds prior to suturing, rather than for extended pain relief in wounds that are likely to remain open to heal by secondary intention. Hence, SURGILUBE™ was not intended to provide a long-lasting barrier (seal) over the open wound, nor was it intended to provide a prolonged analgesic effect due to intrinsic characteristics of the carrier.

The use of topical anesthesia has also been described for pain relief in patients with significant burns (Jellish W S, Gamelli R L, Furry P A, McGill V L, Fluder E M. Effect of topical local anesthetic application to skin harvest sites for pain management in burn patients undergoing skin-grafting procedures. Ann Surg. 1999 January; 229(1):115-20; Brofeldt B T, Cornwell P, Doherty D, Batra K, Gunther R A. Topical lidocaine in the treatment of partial-thickness burns. J Burn Care Rehabil. 1989 January-February; 10(1):63-8). In this situation, the local anesthetic agents (typically lignocaine or EMLA) are applied as creams or solutions which may be covered with a bandage, plastic wrap or gauze to maintain contact with the wound, and can require regular re-application (every 2 to 4 hours if prolonged analgesia is required).

Although topical anesthesia and barrier treatments have been both described in isolation for the management of different aspects of significant open wounds, it has not been previously described to combine the two to achieve a single composition which is capable of acting as the primary mechanism of achieving extended pain relief in significant open wound situations—particularly traumatic or surgically induced cuts, abrasions or lacerations. One of the reasons this has not previously been described is that the need for such a composition was not considered, as many of these wounds occur in animals in whom pain management has been considered a low priority until recently. However, where a need was recognized, the principal reason that the combination was not described was that it was not intuitive. Topical anesthetics were not considered as an option due to their limited duration of action and potential toxicity. Similarly, barrier formulations were not generally considered an option because they are usually rendered ineffective by their inability to adhere to actively bleeding or weeping surfaces, particularly in the acute situation (the first 24-48 hours). In addition, the potential for synergism in analgesic actions with barrier formulations was either not considered or unrecognized as the majority of barrier formulations hinder or block effective absorption of anesthetic agents into a wound by forming an impenetrable coating on the wound surface, on and around exposed nerve tissue.

However, the present inventors made the discovery that some viscous carriers can provide a dual function, in that they can act to promote and/or prolong anesthetic absorption into an open wound as well as provide an effective wound barrier that outlasts the action of the anesthetic agent. The present inventors discovered that the analgesic action of such barrier compositions has the potential to be dramatically improved and thereby contribute to pain reduction in the early, as well as later stages of the wound pain response. This is due to previously unrecognized synergistic interactions between the local anesthetic agent and carrier/barrier.

Trial work by the present inventors revealed that allodynia and early wound hyperalgesia and pain sensitization were prevented or minimized by nerve blockade due to effective action of a topical anesthetic agent. As expected, this effect was enhanced and prolonged (to about 2 hours) by applying a combination of anesthetic agents, with a vasoconstrictor in a slow release carrier such as a viscous gel. In addition, however, the carrier surprisingly exerted its own intrinsic analgesic effect. This is believed to be due to adhesion to the wound and formation of a wound barrier or 'seal' against the environment. In the absence of anesthetic actives this effect became apparent beginning by about 4 hours. Therefore, when used in combination with the anesthetic actives earlier onset, enhanced and prolonged analgesia was achieved due to novel synergistic interactions.

When used in combination with anesthetic actives analgesic effect from the barrier occurred earlier (beginning by 2 hours) than when used alone. It is hypothesized that the absence of wound allodynia, hyperalgesia and sensitization (which occurred as a primary effect of the action of local anesthetic agents) promoted improved potency and earlier onset of analgesia from the wound barrier effect. The analgesic effect of the wound barrier formulation therefore overlapped, enhanced and prolonged the duration of analgesia achieved as a result of the action of the anesthetic actives, and the combined analgesic action exceeded that which may have been anticipated from the actions of either agents alone or in non-synergistic combination.

In addition, a further synergistic effect was achieved due to the enhanced wound healing attributes supplied by such a composition, which had the potential to produce ongoing pain relief by preventing wound crusting, drying and cracking. A final synergistic effect is achieved by the lowered risk of toxicity and enhanced duration of anesthetic effect that is achieved due to the barrier providing controlled release of the anesthetic agent onto the wound.

Trial work by the present inventors also confirmed that toxicity risks of applying topical anesthetic agents to large open wounds are significantly lower than previously thought and remain well below toxic absorption levels despite relatively high dose applications when compared with injected administration. (Karatassas A, Morris R G, Slavotinek A H. The relationship between regional blood flow and absorption of lignocaine. Australian & New Zealand Journal of Surgery. 1993 October; 63(10):766-71; Brofeldt B T, Cornwell P, Doherty D, Batra K, Gunther R A. Topical lidocaine in the treatment of partial-thickness burns. J Burn Care Rehabil. 1989 January-February; 10(1):63-8).

Therefore, the present inventors have discovered novel synergistic interactions that can be harnessed to provide safe and effective topical anesthesia of significant wounds for use in situations where conventional or more intensive or invasive alternatives are unaffordable, impractical or otherwise unavailable.

The novel synergistic combination of topical anesthesia and a wound barrier forming carrier agent has the potential to provide a means of effectively treating pain and improve wound healing in an extremely large number of major open wound situations, both in humans and animals, where previously it was considered that topical anesthesia would have been either too short-lived, too ineffective, or too high a risk of toxicity to be a viable pain management technique and where barrier treatments may otherwise have remained unconsidered.

SUMMARY OF THE INVENTION

According to a first aspect of the present invention, there is provided a topical analgesic composition for use on a significant open wound, said composition comprising at least one local anesthetic agent and a carrier for forming a long-lasting barrier over the open wound, and for promoting and prolonging contact of the anesthetic agent with the wound, wherein the composition provides an analgesic effect beyond that attributable to the anesthetic agent whilst the barrier covers the wound.

According to a first preferred aspect, there is provided a topical analgesic composition for use on a significant open skin wound, said composition comprising at least one local anesthetic agent and a carrier that adheres to the open skin wound, that forms a long-lasting viscous barrier over the open skin wound, and that promotes and prolongs contact of the anesthetic agent with the skin wound, wherein the composition provides an analgesic effect beyond that attributable to the anesthetic agent whilst the barrier covers the skin wound.

According to a second aspect of the present invention, there is provided a method for providing prolonged analgesia to a subject having a significant open wound, said method comprising the step of applying topically to the open wound a composition comprising at least one local anesthetic agent and a carrier for forming a long-lasting barrier over the open wound, and for promoting and prolonging contact of the anesthetic agent with the wound, wherein the composition provides an analgesic effect beyond that attributable to the anesthetic agent whilst the barrier covers the wound.

According to a second preferred aspect, there is provided a method for providing prolonged analgesia to a subject having a significant open skin wound, said method comprising the step of applying topically to the open skin wound a composition comprising at least one local anesthetic agent and a carrier that adheres to the open skin wound, that forms a long-lasting viscous barrier over the open skin wound, and that promotes and prolongs contact of the anesthetic agent with the skin wound, wherein the composition provides an analgesic effect beyond that attributable to the anesthetic agent whilst the barrier covers the skin wound.

According to a third aspect of the present invention, there is provided the use of a composition comprising at least one local anesthetic agent and a carrier in the preparation of a topical medicament for providing prolonged analgesia to a subject having a significant open wound, wherein said carrier forms a long-lasting barrier over the open wound, and promotes and prolongs contact of the anesthetic agent with the wound, and said composition provides an analgesic effect beyond that attributable to the anesthetic agent whilst the barrier covers the wound.

According to a third preferred aspect, there is provided the use of a composition comprising at least one local anesthetic agent and a carrier in the preparation of a topical medicament for providing prolonged analgesia to a subject having a significant open skin wound, wherein said carrier adheres to the open skin wound, forms a long-lasting viscous barrier over the open skin wound, and promotes and prolongs contact of the anesthetic agent with the skin wound, and said composition provides an analgesic effect beyond that attributable to the anesthetic agent whilst the barrier covers the skin wound.

According to a fourth aspect of the present invention, there is provide a method for preparing a topical analgesic composition for use on a significant open wound, wherein said method comprises the step of combining at least one local anesthetic agent together with a carrier for forming a long-lasting barrier over the open wound, and for promoting and prolonging contact of the anesthetic agent with the wound, whereby the composition provides an analgesic effect beyond that attributable to the anesthetic agent whilst the barrier covers the wound.

According to a fourth preferred aspect, there is provide a method for preparing a topical analgesic composition for use on a significant open skin wound, wherein said method comprises the step of combining at least one local anesthetic agent together with a carrier that adheres to the open skin wound, that forms a long-lasting viscous barrier over the open skin wound, and that promotes and prolongs contact of the anesthetic agent with the skin wound, wherein the composition provides an analgesic effect beyond that attributable to the anesthetic agent whilst the barrier covers the skin wound.

The term "significant open wound" is to be understood as including a laceration, surgical incision, ulcer, major abrasion or major burn, but excluding a minor cut, scratch, sting, burn or abrasion. Such a wound is likely to actively bleed or weep.

Likewise, the term "significant open skin wound" is to be understood as excluding a mucous membrane wound of the alimentary and respiratory tracts and eyes, but including a skin laceration, surgical incision, ulcer, major abrasion or major burn and exposed underlying tissues, but excluding a minor cut, scratch, sting, burn or abrasion of the skin.

The term "long-lasting barrier" is to be understood as meaning a barrier/seal that is substantially capable of remaining intact over a significant open wound for hours, days or even weeks, or until the wound has naturally sealed or the pain has otherwise abated by way of the natural healing process.

As mentioned above, the present inventors have found that the analgesic or hypoalgesic effect may be provided for hours, days or even weeks, or until the wound has sealed or the pain has otherwise abated by way of the natural healing process. The barrier has been found to aid in the healing process, presumably by minimizing or preventing water loss from the wound and by acting as a barrier against microbial contamination.

Any suitable carrier can be used. The composition can be applied to the subject in any suitable form, provided that the carrier is able to form a long-lasting barrier over the wound and allow diffusion of actives into the wound.

The composition can be, for example, in form of an ointment, gel, lotion, cream, crème, emulsion, paste, suspension, powder or spray-solution, foam or aerosol. The composition can be incorporated into a bandage or plaster.

Preferably, the carrier is able to: adhere to a weeping or bleeding open skin wound; form a long-lasting viscous barrier over the weeping or bleeding open wound; and promote and prolong contact of the anesthetic agent with the wound. A suitable carrier is preferably capable of also promoting and prolonging contact of other active agents of the composition with the wound.

Preferably, the composition is applied to the subject as a spray-on gel, emulsion, powder, solution, crème, suspension or foam, so as to disturb the wound as little as possible. Preferably, the composition is applied as a metered dose.

The barrier can be, for instance, in the form of a gel, crème or a film. Preferably, the barrier is in the form of a sticky, viscous gel. The carrier can comprise a hydrophilic or hydroalcoholic gelling agent. Preferably, the carrier comprises about 1 to 20 g per liter of at least one type of gum or cellulosic preparation. More preferably, the carrier comprises a polyhydric alcohol in combination with a cellulosic preparation. Even more preferably, the composition comprises about 5 mg/mL hydroxy cellulose in combination with about 100 mg/mL non-crystallizing liquid sorbitol (70%).

The carrier may comprise one or more of the following adhesives, thickening agents, gelling agents and/or viscosity increasing agents: acrylamides copolymer, agarose, amylopectin, calcium alginate, calcium carboxymethyl cellulose, carbomer, carboxymethyl chitin, castor oil derivatives, cellulose gum, cellulosic preparation, cetyl alcohol, cetostearyl alcohol, dextrin, gelatin, hydroxy cellulose, hydroxyethylcellulose, hydroxypropylcellulose, hydroxpropyl starch, inert sugar, magnesium alginate, methylcellulose, microcrystalline cellulose, pectin, PEG's, polyacrylic acid, polymethacrylic acid, polyvinyl alcohol, quaternium ammonium compound of bentonite or zinc stearate, sorbitol, PPG's, sodium acrylates copolymer, sodium carrageenan, xanthum gum, and yeast beta-glucan.

Depending on the form of the composition, the composition can include one or more of the following types of ingredients: aqueous or oily diluent, excipient or base; buffer; bittering agent (i.e. foul-tasting agent); suspending agent; emulsifier; emollient; humectant; stabilizing agent; dispersing agent; solubilizer; skin conditioning agent; skin protectant; skin penetration enhancer; fragrance; preservative; propellant; sunscreen agent; surfactant; textural modifier; and waterproofing agent.

Powders can incorporate a conventional powder base, such as kaolin, lactose, starch or talc.

The propellant can be, for example, a fluorochlorohydrocarbon such as dichlorodifluoromethane, difluoroethane or trichlorofluoromethane.

Any suitable type of anesthetic agent or combination of agents can be used. Lignocaine, chloroprocaine, mepivacaine, bupivacaine, articaine, etidocaine, levobupivacaine, tetracaine, prilocalne, benzocaine, ropivacaine, cocaine, oxyprocaine, hexylcaine, dibucaine, piperocaine and procaine and pharmaceutically acceptable acids, bases and salts thereof, for instance, may be suitable anesthetic agents. Preferably, 2-10 weight/volume % lignocaine is used as the anesthetic agent.

Other potential anesthetic agents include: butamben, butambenpicrate, dimethisoquin hydrochloride, diperodon, diphenhydramine, dyclonine, ketamine, methapyriline, p-buthylaminobenzoic acid, 2-(die-ethylamino) ethyl ester hydrochloride, pramoxine and tripelennamine.

The composition can comprise at least one local anesthetic agent having a rapid onset of action and at least one local anesthetic agent having a long duration of action. Bupivacaine has a much slower onset of action but a much greater duration of action than lignocaine. The composition can comprise 2-10 weight/volume % lignocaine and 0.25-7.5 weight/volume % bupivacaine.

The composition can further include a vasoconstrictor to decrease the rate of vascular absorption of the anesthetic agent, so to improve the depth and duration of anesthesia, to reduce bleeding from the open wound, as well as to reduce systemic toxicity. Any suitable type of vasoconstrictor can be used. Suitable vasoconstrictors include, for instance, adrenaline (epinephrine), noradrenalin (norepinephrine) and fenylpressin. Preferably, the composition includes about 1:1000-1:80,000, more preferably about 1:1000-1:10,000 adrenalin, and even more preferably about 1:2,000 adrenalin.

The composition can include an antioxidant or a preservative, such as sodium metabisulfite. Any suitable amount of sodium metabisulfite can be used, e.g. up to about 3.5 mg/mL.

The composition can further include an emollient. An emollient can prevent water loss and can have a softening and soothing effect on the skin. Some examples of emollients are: acetyl arginine, acetylated lanolin, algae extract, apricot kernel oil PEG-6 esters, avocado oil PEG-11 esters, bis-PEG-4 dimethicone, butoxyethyl stearate, C18-C36 acid glycol ester, C2-C13 alkyl lactate, caprylyl glycol, cetrimide, cetyl esters, cetyl laurate, coconut oil PEG-10 esters, di-C12-C13 alkyl tartrate, diethyl sebacate, dihydrocholesteryl butyrate, dimethiconol, dimyristyl tartrate, disteareth-5 lauroyl glutamate, ethyl avocadate, ethylhexyl myristate, glyceryl isostearates, glyceryl oleate, hexyldecyl stearate, hexyl isostearate, hydrogenated palm glycerides, hydrogenated soy glycerides, hydrogenated tallow glycerides, hydroxypropyl bisisostearamide MEA, isostearyl neopentanoate, isostearyl palmitate, isotridecyl isononanoate, laureth-2 acetate, lauryl polyglyceryl-6 cetearyl glycol ether, methyl gluceth-20 benzoate, mineral oil, myreth-3 palmitate, octyldecanol, octyldodecanol, odontella aurita oil, 2-oleamido-1,3 octadecanediol, palm glycerides, PEG avocado glycerides, PEG castor oil, PEG-22/dodecyl glycol copolymer, PEG shorea butter glycerides, phytol, raffinose, stearyl citrate, sunflower seed oil glycerides and tocopheryl glucoside.

The composition can include one or more other active ingredients. An active ingredient, as defined herein, is a compound that provides benefit to the subject. The active ingredient can be, for instance, an antibody, analgesic, anticoagulant, antiproliferative, anti-inflammatory, cytokine, cytotoxin, growth factor, interferon, haemostatic agent, hormone, lipid, demineralized bone or bone morphogenetic protein, cartilage inducing factor, oligonucleotide, polymer, polysaccharide, polypeptide, protease inhibitor, vitamin, mineral, antiseptic agent, insecticide or insect repellent, antibiotic or antifungal agent.

Potential analgesic anti-inflammatory agents include the following: acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexemacpiroxicam, phenylbutazone, oxyphenbutazone, clofezone, pentazocine, mepirizole, hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, and tolmetin.

The composition preferably includes an antiseptic agent to, amongst other things, minimize wound contamination and infection. Any suitable type of antiseptic agent can be used. Suitable antiseptic agents include cetrimide, povidone-iodine, chlorhexidine, iodine, benzalkonium chloride, benzoic acid, nitrofurazone, benzoyl peroxide, hydrogen peroxide, hexachlorophene, phenol, resorcinol and cetylpyridinium chloride. The composition preferably includes cetrimide within a range of about 0.5% w/v to about 5% w/v.

The composition preferably includes an insecticide or insect repellent to stop insects from infesting the open wound. Any suitable type of insecticide or insect repellent can be used. Examples of suitable insecticides include: trichlorfon, triflumeron, fenthion, bendiocarb, cyromazine, dislubenzuron, dicyclanil, fluazuron, amitraz, deltamethrin, cypermethrin, chlorfenbinphos, flumethrin, ivermectin, abermectin, avermectin, doramectin, moxidectin, zeti-cypermethrin, diazinon, spinosad, imidacloprid, nitenpyran, pyriproxysen, sipronil, cythioate, lufenuron, selamectin, milbemycin oxime, chlorpyrifos, coumaphos, propetamphos, alpha-cypermethrin, high cis cypermethrin, ivermectin, diflubenzuron, cyclodiene, carbamate and benzoyl urea.

The composition can include a detectable marker for indicating the presence of the composition on the wound. Any suitable type of detectable marker can be used. The marker may be, for instance, visible to the eye or visible under UV light. The detectable marker is preferably a visual marker and can be visible either before the composition is applied to the subject and/or after the composition is applied to the subject. The detectable marker is preferably a colorant. The colorant can be a pigment and/or dye. Suitable colorants include, for example, common food dyes or the ORCODERM®, ORCO-BRITE® and ORCOFUR® lines of pigments and dyes sold by the Organic Dyestuffs Corporation. Preferably, the detectable marker is non-toxic and will not permanently stain the skin or animal hide or surrounding hair, fur or wool.

The composition can include a skin penetration enhancer for enhancing the penetration of active ingredients, such as the anesthetic agent. Any suitable type of enhancer can be used. Examples of suitable enhancers may include solvents, detergents or low carbon alcohols such as dimethylsulfoxide, oleyl alcohol, propylene glycol, methyl pyrrolidone and dodecylazyl cycloheptan 2-one.

The subject can be a human. The subject can be an animal such as a sheep, horse, cow, goat, pig, dog or cat. The subject can be another type of mammal or animal.

The composition can be used for an animal husbandry procedure. The procedure can be, for example, mulesing, shearing, castration, tail docking, ear tagging, de-horning, branding or marking. Preferably, the composition is used for mulesing which is performed so as to prevent flystrike.

According to a fourth aspect of the present invention, there is provided a topical analgesic composition for use on a significant open wound such as a laceration, a surgical incision, an ulcer, a major abrasion or a major burn, said composition comprising:
  at least one local anesthetic agent;
  a carrier comprising a hydrophilic or hydroalcoholic gelling agent for forming a long-lasting barrier over the open wound;
  optionally, an antiseptic agent; and
  a vasoconstrictor.

According to a fourth preferred aspect, there is provided a topical analgesic composition for use on a significant open skin wound such as a laceration, a surgical incision, an ulcer, a major abrasion or a major burn, said composition comprising:
  at least one local anesthetic agent;
  a carrier comprising a hydrophilic or hydroalcoholic gelling agent that adheres to the open skin wound, that forms a long-lasting viscous barrier over the open skin wound, and that promotes and prolongs contact of the anesthetic agent with the skin wound; and
  a vasoconstrictor,
  wherein the composition provides an analgesic effect beyond that attributable to the anesthetic agent whilst the barrier covers the skin wound.

According to a fifth aspect of the present invention, there is provided a method for providing prolonged analgesia to a subject having a significant open wound such as a laceration, a surgical incision, an ulcer, a major abrasion or a major burn, said method comprising the step of applying topically to the open wound a composition comprising:
  at least one local anesthetic agent;
  a carrier comprising a hydrophilic or hydroalcoholic gelling agent for forming a long-lasting barrier over the open wound;
  an antiseptic agent; and
  a vasoconstrictor.

According to a fifth preferred aspect, there is provided a method for providing prolonged analgesia to a subject having a significant open skin wound such as a laceration, a surgical incision, an ulcer, a major abrasion or a major burn, said method comprising the step of applying topically to the open skin wound a composition comprising:
  a carrier comprising a hydrophilic or hydroalcoholic gelling agent that adheres to the open skin wound, that forms a long-lasting viscous barrier over the open skin wound, and that promotes and prolongs contact of the anesthetic agent with the skin wound; and
  a vasoconstrictor,
  wherein the composition provides an analgesic effect beyond that attributable to the anesthetic agent whilst the barrier covers the skin wound.

The composition according to the fourth and fifth aspects can comprise one or more ingredients as mentioned elsewhere in this specification, e.g.: an antioxidant; an antiseptic agent; a detectable marker for indicating the presence of the composition on the open wound; a local anesthetic agent having a rapid onset of action and a local anesthetic agent having a long duration of action.

In a first preferred embodiment, the composition comprises:
  about 100 mg/mL non-crystallizing liquid sorbitol (70%);
  about 50.0 mg/mL lignocaine HCl;
  about 5.0 mg/mL bupivacaine HCl;
  about 1.5 mg/mL sodium metabisulfite;
  about 0.5 mg/mL to 5.0 mg/mL cetrimide;
  about 45.0 µg/mL adrenaline tartrate;
  about 5.0 mg/mL hydroxy cellulose; and
  dye.

In a second preferred embodiment, the composition comprises:
  about 100 mg/mL non-crystallizing liquid sorbitol (70%);
  about 40.0 mg/mL lignocaine HCl;
  about 1.5 mg/mL sodium metabisulfite;
  about 0.5 mg/mL to 5.0 mg/mL cetrimide;
  about 36.0 µg/mL adrenaline tartrate;
  about 5.0 mg/mL hydroxy cellulose; and
  dye.

When the composition is used on animals, such as for mulesing, the composition preferably includes an insecticide or insect repellent. If used for, say, castration or tail docking, the composition may include a penetration enhancer.

Accordingly, in a sixth aspect of the present invention, there is provided a method for providing prolonged analgesia to a subject having a significant open wound caused by mulesing, said method comprising the step of applying topically to the open wound a composition comprising at least one local anesthetic agent and a carrier for forming a long-lasting barrier over the open wound, and for promoting and prolonging contact of the anesthetic agent with the wound, wherein the composition provides an analgesic effect beyond that attributable to the anesthetic agent whilst the barrier covers the wound.

According to a sixth preferred aspect, there is provided a method for providing prolonged analgesia to a subject having a significant open wound caused by mulesing, said method comprising the step of applying topically to the open wound a composition comprising at least one local anesthetic agent and a carrier that adheres to the open wound, that forms a long-lasting viscous barrier over the open wound, and that promotes and prolongs contact of the anesthetic agent with the wound, wherein the composition provides an analgesic effect beyond that attributable to the anesthetic agent whilst the barrier covers the skin wound.

Preferably, the composition comprises: a local anesthetic agent having a rapid onset of action; a local anesthetic agent having a long duration of action; a carrier comprising a hydrophilic or hydroalcoholic gelling agent; an antiseptic agent; a vasoconstrictor; an antioxidant; a detectable marker for indicating the presence of the composition on the open wound; and, an insecticide or insect repellent.

Accordingly, in a seventh aspect of the present invention, there is provided a method for providing prolonged analgesia to a subject having a significant open wound caused by castration, said method comprising the step of applying topically to the open wound a composition comprising at least one local anesthetic agent and a carrier for forming a long-lasting barrier over the open wound, and for promoting and prolonging contact of the anesthetic agent with the wound, wherein the composition provides an analgesic effect beyond that attributable to the anesthetic agent whilst the barrier covers the wound.

According to a preferred seventh aspect, there is provided a method for providing prolonged analgesia to a subject having a significant open wound caused by castration, said method comprising the step of applying topically to the open wound a composition comprising at least one local anesthetic agent and a carrier that adheres to the open wound, that forms a long-lasting viscous barrier over the open wound, and that promotes and prolongs contact of the anesthetic agent with the wound, wherein the composition provides an analgesic effect beyond that attributable to the anesthetic agent whilst the barrier covers the wound.

Preferably, the composition comprises ingredients as listed in respect of the sixth aspect, as well as a penetration enhancer.

According to an eighth aspect of the present invention, there is provided a topical composition for both creating a significant open wound on a subject and for alleviating pain due to the open wound, said composition comprising: at least one wounding agent for creating an open wound; at least one local anesthetic agent for anaesthetizing the open wound; and a carrier for forming a long-lasting barrier over the open wound, and for promoting and prolonging contact of the anesthetic agent with the wound, wherein the composition provides an analgesic effect beyond that attributable to the anesthetic agent whilst the barrier covers the wound.

According to a ninth aspect of the present invention, there is provided a method for both creating a significant open wound on a subject and for alleviating pain due to the open wound, said method comprising the step of applying topically to the subject a composition comprising: at least one wounding agent for creating an open wound; at least one local anesthetic agent for anaesthetizing the open wound; and a carrier for forming a long-lasting barrier over the open wound, and for promoting and prolonging contact of the anesthetic agent with the wound, wherein the composition provides an analgesic effect beyond that attributable to the anesthetic agent whilst the barrier covers the wound.

The composition can be used for any suitable type of procedure in which skin, wool, fur or hair removal is required. The procedure can be, for example, chemical mulesing or branding of an animal. Preferably, the composition is used for chemical mulesing.

The wounding agent can be, for instance, a defleecing agent or skin scarring agent that causes temporary or permanent defleecing/wool or hair follicle destruction/skin scarring at the site of application.

The defleecing/scarring agent can comprise, for instance, one or more of the following: phenol; and, a cationic quaternary ammonium compound having the formula:

wherein R1 and R2 are alkyl having 8-10 carbon atoms, examples being didecylmethylamine oxide, didecyldimethylammonium chloride, dioctyldimethylammonium chloride, octyldecyldimethylammonium chloride, didecyldimethylammonium chloride, didecylmethylethylammonium chloride, didecylmethylpropylammonium chloride, didecylethylpropylammonium chloride, nonyltrimethylammonium bromide, tricapryl(trioctyl)methylammonium chloride, trioctylpropylammonium bromide, and Adogen 464-trimethyl C8-C10 quaternaryammonium chloride.

Further defleecing/scarring agents are described in the specifications of Australian Patent No. 524658 to ICI Australia Limited and No. 647784 to Commonwealth Scientific and Industrial Research Organisation—the entire contents of which are hereby incorporated by reference.

Any suitable quantity of defleecing/scarring agent or agents can be used. If the composition contains phenol, then it can comprise about 25-80% weight/volume of that compound. The phenol can be phenol, resorcinol or cresol, or a mixture of those compounds. The composition can include other ingredients as described in the specification of No. 524658.

If the composition contains a cationic quaternary ammonium compound, then it can comprise about 15-25% weight/weight of that compound. The composition can include other ingredients as described in the specification of No. 647784.

The composition can comprise other ingredients as described in respect of the other aspects of the invention.

Having broadly described the invention in its various embodiments, non-limiting examples of embodiments will now be given.

DETAILED DESCRIPTION OF THE INVENTION

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide a method for preparing a topical analgesic composition for use on a significant open skin wound.

Example 1

Formulation of a Topical Analgesic Gel for Open Wounds Having a Long Duration of Action This example describes the preparation of a particularly preferred topical analgesic composition for the management of significant open wounds. The composition is in the form of a spray-on gel that provides a prolonged analgesic effect. The composition has the following formulation:

| | |
|---|---|
| Purified water Sorbitol Liquid 70% Non-Crystallizing | 100.0 mg/mL |
| Lignocaine HCl | 50.0 mg/mL (5%) |
| Bupivacaine HCl | 5.0 mg/mL (0.5%) |
| Sodium Metabisulfite | 1.5 mg/mL |
| Cetrimide | 0 mg/mL-5.0 mg/mL |
| Adrenaline Tartrate | 45.0 µg/mL |
| Food Dye (e.g. brilliant blue) | Quantity to suit (q.s.) |
| Hydroxy Cellulose | 5.0 mg/mL |
| Purified water | to 1 mL |

The composition is prepared by combining the above ingredients to achieve the required color and consistency as required. The composition is then placed within a suitable spray-on applicator. The composition is viscous and, when applied, is in the form of a "sticky" gel.

Sorbitol functions as a thickener and a humectant and keeps the gel "sticky" after application. Sodium metabisulfite prevents oxidation of the adrenalin. Cetrimide is an antiseptic as well as a surfactant and humectant. Hydroxy cellulose functions as a thickener.

The gel is capable of forming a barrier (seal) over the wound and can provide sustained release of the anesthetic agents to the nerve endings of the wound. The gel can maintain the actives, such as the anesthetic agents, the vasoconstrictor (adrenaline) and the antiseptic agent (cetrimide), at the wound site. The gel can serve as a barrier against microbes. The gel is a humectant and, together with the cetrimide, keeps the wound moist. Depending on the consistency of the gel, the gel could remain intact over the wound for hours, days, or possibly up to a week.

The hydroxy cellulose and sorbitol together serve as a carrier for the actives and are primarily responsible for the gelatinous nature of the composition. Although typically the composition will comprise about 5 mg/mL hydroxy cellulose in combination with about 100 mg/mL non-crystallizing liquid sorbitol (70%), the carrier can comprise anywhere from about 1 to 20 g per liter of at least one type of gum or cellulosic preparation. Typically, the composition will comprise a polyhydric alcohol in combination with a cellulosic preparation.

If desired, the composition can further comprise an anti-inflammatory agent (e.g. isoflupredone acetate), and/or an insecticide/insect repellent such as diazinon, spinosad or cyromazine (at about 1 mg/mL), and/or a skin penetrating enhancer, and/or a bittering agent.

Example 2

Formulation of a Topical Analgesic Gel for Open Wounds

This example describes the preparation of another preferred topical analgesic composition for the management of significant open wounds. The composition is in most respects the same as the composition of Example 1, except that it excludes bupivacaine. The composition has the following formulation:

| | |
|---|---|
| Purified water Sorbitol Liquid 70% Non-Crystallizing | 100.0 mg/mL |
| Lignocaine HCl | 40.0 mg/mL (4%) |
| Sodium Metabisulfite | 1.5 mg/mL |
| Cetrimide | 0 mg/mL-5.0 mg/mL |
| Adrenaline Tartrate | 36.0 µg/mL (1:2000) |
| Food Dye (e.g. blue) | q.s. |
| Hydroxy Cellulose | q.s. |
| Purified water | to 1 mL |

The composition is prepared by combining the above ingredients to achieve the required color and consistency as required. The composition is then placed within a suitable spray-on applicator. The composition is viscous and, when applied, is in the form of a "sticky" gel. Typically, the composition will comprise about 5 mg/mL hydroxy cellulose in combination with about 100 mg/mL non-crystallizing liquid sorbitol (70%).

If desired, the composition can further comprise an insecticide/insect repellent such as cyromazine or spinosad (at about 1 mg/mL) and/or a skin penetrating enhancer.

Example 3

Use of the Composition of Example 1 in Mulesing

This example describes the use of the composition of Example 1 in a mulesing trial.

If necessary, the breech area of the sheep is crutched of wool. Mulesing is then performed. This involves removing strips of skin from either side of the perineum and from the dorsal surface of the tail. The tail may be docked at the same time. The composition is then immediately applied to the surgical wound as a colored gel by a metered dose spray-on pump pack or trigger spray bottle. The agent is applied in an adequate volume to effectively cover the open wound surface. Between 5-15 mLs of the composition is applied depending on lamb weight and wound size.

The results of the trial are discussed hereafter.

Significant ($p<0.05$) induction of wound anesthesia (as demonstrated by absence or reduction of the incidence of allodynia and wound hyperalgesia and reduced pain related behavior responses) occurred in an 8 hour monitored period following routine mulesing in 2 to 5 month old lambs when treated with the anesthetic composition containing lignocaine 5% bupivacaine 0.5% with adrenalin 1:2000 and cetrimide (antiseptic) in a tenacious viscous gel carrier designed to provide prolonged adhesion to wound surface, prolonged anesthetic diffusion and emollient wound coating. This was as opposed to findings of marked and prominent wound hyperalgesia which developed in 83% of untreated lambs during the same 8 hour monitoring period following the procedure.

A significant (p<0.05) reduction in wound allodynia and hyperalgesia also occurred in lambs treated with a placebo gel (containing the same viscous gel carrier as above, without anesthetic or vasoconstrictor agents) when compared with untreated lambs 4 hours (but not 1-2 hours) following the procedure. This indicated that a significant intrinsic pain relieving effect of the carrier alone, due to wound coating and emollient properties had developed after a 4 hour period.

A reduction in the incidence of pain related behavior was also observed 24 hours and 7 days following the procedure in treated as opposed to untreated lambs with prevention of a mean 10% weight loss over a 2 week period in treated lambs. This provided evidence that prolonged and extended pain relief/reduction (beyond that attributable to action of anesthetic agents) occurred following a single topical application of the composition. There was also evidence of improved wound healing, with less cracking, crusting, and ulceration of wounds in treated as opposed to untreated lambs. Significant improvement in wound healing was also evident in treated versus untreated lambs based on the rate of reduction of wound surface area. Total wound surface area had reduced by 70% (treated) versus 60% (untreated) two weeks post-mulesing (p=0.01) and 90% (treated) versus 80% (untreated) 4 weeks post mulesing (p=0.04) in a mob of 60 treated versus 60 untreated 2 to 4 month old lambs. For those lambs examined, the barrier remained visible on the wound for at least 8 hours.

The synergistic interaction between anesthetic agents and vasoconstrictors has previously been described, as has the interaction between anesthetic agents and carriers. However, at present, such interaction is only believed effective at prolonging the duration of topical local analgesia from around 30 minutes to a maximum of 2 hours when used in topical applications on open wounds. If used alone, (without covering or repeat application) the development of pain and wound hyperalgesia would be anticipated after this period based on this interaction alone.

The composition as exemplified herein has novel synergistic properties that relate to interaction between anesthetic agent, vasoconstrictor, slow-release carrier and wound barrier formation for use in the acute open wound situation. The early and initial pain relief, provided by the effect of local anesthetic agents on nerve fibers also reduces the development of wound hyperalgesia and pain sensitization. This, in turn, improves and enhances the pain relief achieved due to the wound sealing and barrier function of the carrier after the anesthetic action wears off—thereby exceeding that that could be achieved using either the anesthetic agents or the barrier solution alone.

Ongoing and extended pain relief is also supplied by the enhanced wound healing properties supplied by the combination of gel carrier, vasoconstrictor and anesthetic agent which prevents crusting, cracking and/or heavy scab formation and moistens the wound—all of which promote and speed natural epithelial regeneration and natural granulation and wound healing.

The figures are graphical representations of pain abatement in both untreated and treated significant open wounds. The X-axis represents, in hours, the time from injury. The Y-axis represents percentage wound anesthesia, wherein 100% signifies complete wound anesthesia.

Figure 1:
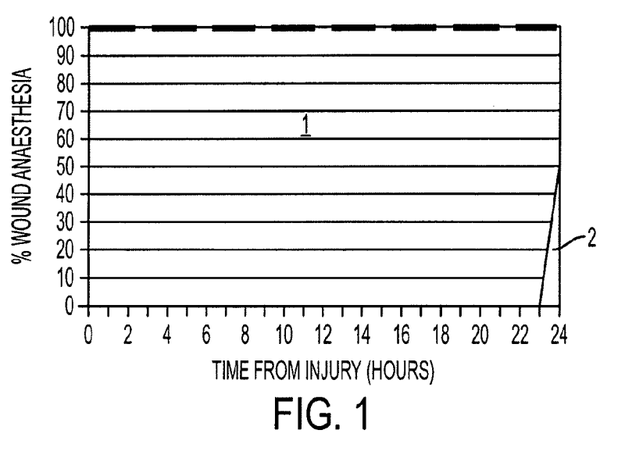
FIG. 1 is a graphical representation of pain abatement for an untreated significant open wound.

Referring first to FIG. 1, there is shown a graphical representation of pain abatement in an untreated significant open wound. Wound pain is represented by an area marked '1'.

Wound pain begins to abate after about 24-48 hours due to reduced inflammation and natural wound sealing, and is represented by an area marked '2'.

Figure 2:
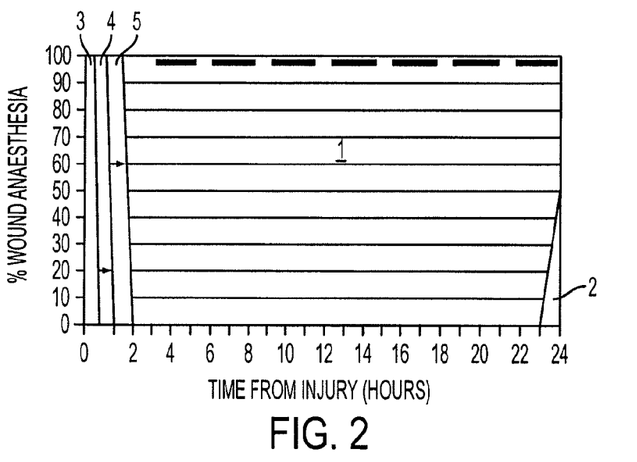
FIG. 2 relates to the graphical representation of FIG. 1 but further shows pain abatement due to treatment of the wound with lignocaine '3', lignocaine plus a vasoconstrictor '4', and, lignocaine plus a vasoconstrictor and a long acting anesthetic in a slow release carrier '5'.

FIG. 2 is the same as FIG. 1 but further showing pain abatement due to treatment of the wound with various local anesthetic combinations. Area '1' denotes wound pain. Area '2' denotes abatement in wound pain due to natural wound sealing. Area '3' denotes the effect of lignocaine alone. Lignocaine alone provides anesthesia for around 30 minutes. Area '4' denotes the effect of lignocaine in combination with a vasoconstrictor. This combination doubles the duration of anesthesia due to lignocaine alone to about 1 hour. Area '5' denotes the effect of lignocaine plus a vasoconstrictor and a long acting anesthetic (such as bupivacaine) in a slow release carrier. This combination extends the duration of topical anesthesia to about 2 hours.

Figure 3:
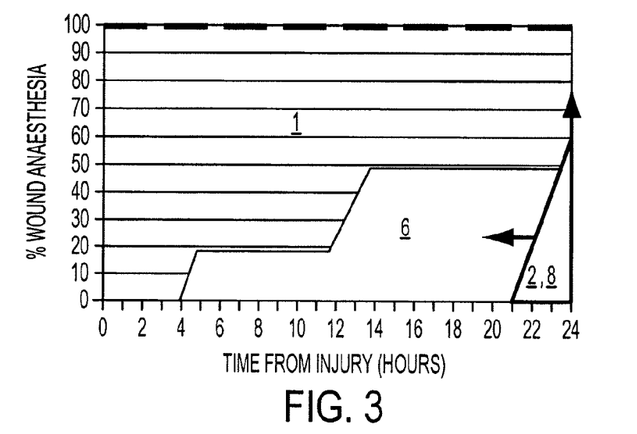
FIG. 3 relates to the graphical representation of FIG. 1 but further shows pain abatement due to the use of an agent/carrier that forms a barrier/seal over the wound.
Figure 4:
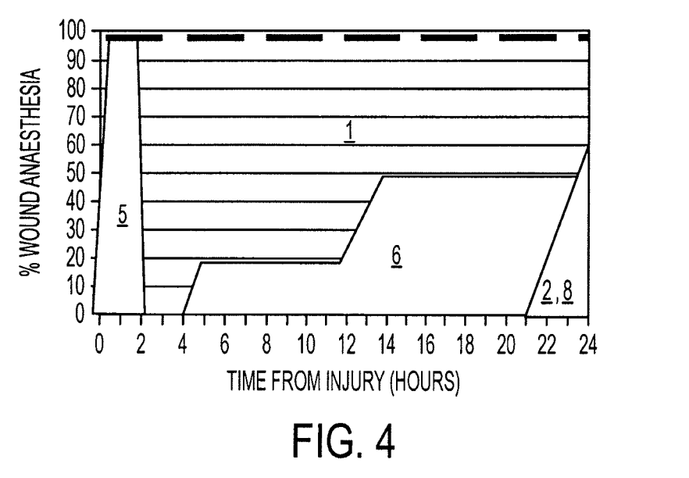
FIG. 4 relates to the graphical representations of FIGS. 2 and 3, and shows predicted pain abatement due to the use of the agent/carrier in combination with lignocaine combination '5' of FIG. 2.

FIG. 3 is the same as FIG. 1 but further shows pain abatement due to the use of an agent/carrier that forms a barrier/seal over the wound. Area '1' denotes wound pain. Area '6' denotes the analgesic effect due to the barrier action of the agent/carrier. The barrier has minimal effect during the acute nerve stimulation phase of injury and early inflammatory response. The barrier has a later effect in that it coats nerve fibers, protects the wound from drying out and from ongoing interaction with the external environment. Area '2', '8' denotes abatement in wound pain due to natural wound sealing. The analgesic effect is due to inflammation subsiding and natural wound sealing. This occurs earlier and is enhanced due to the barrier action of the carrier. FIG. 4 is the same as FIGS. 2 and 3 but shows predicted pain abatement due to the use of the agent/carrier in combination with lignocaine combination '5' of FIG. 2. Area '1' denotes wound pain. Area '6' denotes the analgesic effect due to the barrier action of the agent/carrier. Area '5' denotes the analgesic effect due to lignocaine combination '5'. Area '2', '8' denotes abatement in wound pain due to natural wound sealing.

Figure 5:
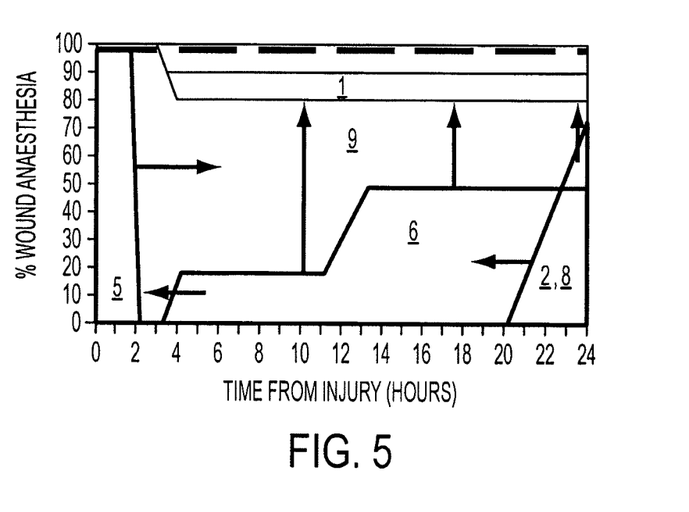
FIG. 5 relates to the graphical representation of FIG. 4 but shows the newly discovered synergistic effects of the agent/carrier and anesthetic combination '5'.

FIG. 5 is the same as FIG. 4 but shows the newly discovered (unexpected) synergistic effects due to the use of the agent/carrier in combination with lignocaine combination '5'. Area '1' denotes wound pain. Area '6' denotes the analgesic effect due to the barrier action of the agent/carrier. This is enhanced due to reduced nerve sensitization. Area '5' denotes the analgesic effect due to lignocaine combination '5'. This is extended by the barrier action reducing ongoing nerve stimulation. Area '2', '8' denotes abatement in wound pain due to natural wound sealing. This occurs earlier due to barrier protection or reduced nerve sensitization.

Example 4

Formulation of a Topical Anesthetic Crème Having a Long Duration of Action

This example describes the preparation of another topical anesthetic composition in the form of a spray-on crème. The composition has the following formulation:

| | |
|---|---|
| Cetyl Alcohol | 78.00 mg/mL |
| Paraffin Wax | 135.00 mg/mL |
| Glycerol | 75.00 mg/mL |
| Lauryl Sulfate | 10.00 mg/Ml |
| Dye | q.s. |
| Lignocaine HCl | 50.00 mg/mL |
| Bupivacaine HCl | 5.00 mg/mL |
| Sodium Metabisulfite | 1.50 mg/mL |
| Cetrimide | 0 mg/mL-5.00 mg/mL |
| Hydrochloric Acid 25% | q.s. |

-continued

| | |
|---|---|
| Adrenaline Acid Tartrate | 0.045 mg/mL |
| Purified Water | to 1 mL |

The composition is prepared by combining the above ingredients to achieve the required color and consistency as required. The composition is then placed within a suitable spray-on applicator. The composition is in the form of a "sticky" crème.

If desired, the composition can further comprise an anti-inflammatory agent, and/or an insecticide/insect repellent, and/or a skin penetrating enhancer, and/or a bittering agent.

Example 5

Formulation of a Topical Anesthetic Gel Having a Long Duration of Action

This example describes the preparation of another topical anesthetic composition in the form of a spray-on gel having a gum base. The composition has the following formulation:

| | |
|---|---|
| Xanthum Gum | 10.00 mg/mL |
| Gum Arabic | 1.00 mg/mL |
| Sorbitol Liquid | 100.00 mg/mL |
| Dye | q.s. |
| Lignocaine HCl | 50.00 mg/mL |
| Bupivacaine HCl | 5.00 mg/mL |
| Sodium Metabisulfite | 1.50 mg/mL |
| Cetrimide | 0 mg/mL-5.00 mg/mL |
| Hydrochloric Acid 25% | q.s. |
| Adrenaline Acid Tartrate | 0.045 mg/mL |
| Purified Water | to 1 mL |

The composition is prepared by combining the above ingredients to achieve the required color and consistency as required. The composition is then placed within a suitable spray-on applicator. The composition is in the form of a "sticky" gel.

If desired, the composition can further comprise an anti-inflammatory agent, and/or an insecticide/insect repellent, and/or a skin penetrating enhancer, and/or a bittering agent.

Example 6

Formulation of a Topical Anesthetic Gel Having a Long Duration of Action

This example describes the preparation of another topical anesthetic composition in the form of a spray-on gel having a polyacrylic acid base. The composition has the following formulation:

| | |
|---|---|
| Polyacrylic Acid | 10.00 mg/mL |
| Sodium Hydroxide | q.s. |
| Polyhydrogenated Castor Oil | 10.00 mg/mL |
| Sorbitol Liquid | 100.00 mg/mL |
| Dye | q.s. |
| Lignocaine HCl | 50.00 mg/mL |
| Bupivacaine HCl | 5.00 mg/mL |
| Sodium Metabisulfite | 1.50 mg/mL |
| Cetrimide | 0 mg/mL-5.00 mg/mL |
| Hydrochloric Acid 25% | q.s. |
| Adrenaline Acid Tartrate | 0.045 mg/mL |
| Purified Water | to 1 mL |

The composition is prepared by combining the above ingredients to achieve the required color and consistency as required. The composition is then placed within a suitable spray-on applicator. The composition is in the form of a "sticky" gel.

If desired, the composition can further comprise an anti-inflammatory agent, and/or an insecticide/insect repellent, and/or a skin penetrating enhancer, and/or a bittering agent.

Example 7

Formulation of a Topical Anesthetic Gel Having an Insecticide and a Skin Penetrating Enhancer This example describes the preparation of another topical anesthetic composition in the form of a spray-on gel having an insecticide (spinosad) as well as a skin penetrating enhancer (propylene glycol). The composition has the following formulation:

| | |
|---|---|
| Cellulose | 5.00 mg/mL |
| Spinosad | 1.25 mg/mL |
| Propylene Glycol | 100.00 mg/mL |
| Sorbitol Liquid | 50.00 mg/mL |
| Dye | q.s. |
| Lignocaine HCl | 50.00 mg/mL |
| Bupivacaine HCl | 5.00 mg/mL |
| Sodium Metabisulfite | 1.50 mg/mL |
| Cetrimide | 0 mg/mL-5.00 mg/mL |
| Hydrochloric Acid 25% | q.s. |
| Adrenaline Acid Tartrate | 0.045 mg/mL |
| Purified Water | to 1 mL |

The composition is prepared by combining the above ingredients to achieve the required color and consistency as required. The composition is then placed within a suitable spray-on applicator. The composition is in the form of a "sticky" gel.

If desired, the composition can further comprise an anti-inflammatory agent, and/or a bittering agent.

Optimally, in use, the composition is applied directly onto the wound and onto the woolen skin surrounding the wound/cut skin edges for a distance of about 2-10 cm.

Example 8

Use of a Topical Anesthetic Composition for Castration

This example describes the use of the composition of any one of Examples 1, 2, and 4 to 7, but preferably Example 1 (if fly/insect infestation risk is low) or 7 (if fly/insect infestation risk is high), for animal castration.

The animal should be held firmly and securely in a cradle or restraint designed for routine surgical castration. An incision is made in the scrotal sac and the testes and chordal tissue exposed as per routine surgical castration. The composition is then sprayed onto the chordal tissue so as to fully coat it, particularly at the site of intended incision and along the length of chordal tissue that will remain and retract into the scrotal sac after the testes are excised. Depending on the size of the animal, approximately 0.5-2 mLs of spray-on composition is used. The testes are then excised by cutting through the chordal tissue at the level where the composition has been applied, using routine surgical castration technique. The empty scrotal sac and edges of the skin incision are then sprayed with an additional dose of the composition so as to fill the sac and coat the cut skin edges. Depending on the size of the animal, approximately 1-4 mLs of spray-on composition is used.

Example 9

Use of a Topical Anesthetic Composition for Shearing Cuts, Skin Lacerations and Superficial Burns This example describes the use of the composition of any one of Examples 1, 2 and 4-7 for shearing cuts, skin lacerations and burns.

Where a significant skin laceration or superficial (1st or second degree) burn occurs, such as during shearing or branding, the composition may be sprayed directly onto the wound so as to coat the wound and cover the cut skin edges +/- the woolled or furred skin surrounding the wound for a distance of 2-10 cm for insecticide containing preparations. The spray is applied by metered dose. The volume applied will vary depending on the size of the wound and animal. For instance, a total dose of 50 mg/kg of lignocaine should not be exceeded for sheep.

Example 10

Use of a Topical Anesthetic Composition for Dehorning

This example describes the use of the composition of any one of Examples 1, 2 and 4-7 for dehorning.

Where dehorning of animals is carried out leaving a raw, bleeding bed of tissue, the composition may be applied directly to the raw tissue bed immediately following dehorning either by metered spray, or by metered squeeze application of the composition in a thick gel, crème or paste so as to cover the entire exposed tissue bed and remain in contact with it. Estimated volumes required are 1-3 mLs per dehorned tissue bed depending on the size of the wound. The total dose applied should not exceed safety limits of mg/kg lignocaine (topically applied) for the animal species involved.

Example 11

Use of a Topical Anesthetic Composition for Treating Flystrike Wounds

This example describes the use of a topical anesthetic composition containing an insecticide, such as the composition described in Example 7, for treating wounds resulting from flystrike.

Flystrike wounds are very painful for sheep. Current practices involve cutting away all wool in the flystruck area and then spraying or applying an insecticide to kill the maggots and eggs. Pain is not addressed. A combination agent of a maggot killing insecticide plus an anesthetic agent, such as the composition described in Example 6, may be applied to kill maggots and relieve pain and aid in wound healing.

The method entails cutting wool away from an affected area and scraping maggots off as per routine flystrike management. The composition is sprayed by metered dose to cover the affected area. The volume applied will vary depending on the size of the wound and animal. For instance, a total dose of 50 mg/kg of lignocaine should not be exceeded for sheep. In cases of large flystrike wounds where it is anticipated that an excessive volume of the composition is required to cover the wound (e.g. >1 ml/kg/sheep), a lower concentration composition should be used containing, for example, 1 or 2% lignocaine with insecticide.

Example 12

Formulation of Topical Analgesic Compositions for Chemical Mulesing or Branding This example describes various compositions for use in chemical mulesing or branding.

Each composition for use in chemical mulesing or branding includes a wounding agent, such as a cationic quaternary ammonium compound, in combination with one or more anesthetic agents as described in the above examples.

Various formulations are given below:

1. Dimethyl Ammonium Chlorides with Emollients

| | |
|---|---|
| Dimethyl Ammonium Chlorides | 250.00 mg/mL |
| Propylene Glycol | 150.00 mg/mL |
| Sorbitol Liquid | 100.00 mg/mL |
| Dye | q.s. |
| Glycerol | 400.00 mg/mL |
| Purified Water | to 1 mL |

This mixture is then admixed with, say, the composition of Example 1 or 2.

2. Dimethyl Ammonium Chlorides in a Crème Base

| | |
|---|---|
| Dimethyl Ammonium Chlorides | 250.00 mg/mL |
| Cetyl Alcohol | 80.00 mg/mL |
| Propylene Glycol | 100.00 mg/mL |
| Dye | q.s. |
| Purified Water | to 1 mL |

This mixture is then admixed with, say, the composition of Example 1 or 2.

3. Dimethyl Ammonium Chlorides in Polyacrylic Acid Base

| | |
|---|---|
| Dimethyl Ammonium Chlorides | 250.00 mg/mL |
| Polyacrylic Acid | 10.00 mg/mL |
| Sodium Hydroxide | q.s. |
| Propylene Glycol | 100.00 mg/mL |
| Dye | q.s. |
| Purified Water | to 1 mL |

This mixture is then admixed with, say, the composition of Example 1 or 2.

Each chemical mulesing/branding composition is prepared by combining the above ingredients to achieve the required color and consistency as required. The composition is then applied against the skin with a squeeze-on applicator which is combed through the wool/fur over the required skin area. The composition is viscous and, when applied, is in the form of a "sticky" base. The ammonium compound, where applied, creates a wound, and shortly thereafter the wound is anaesthetized as described in Example 3.

If desired, the composition can further comprise an insecticide/insect repellent such as cyromazine or spinosad (at about 1 mg/mL) and/or a skin penetrating enhancer.

Advantages of the present invention as exemplified include that the analgesic composition can be used to reduce or minimize pain in a large variety of procedures in which anesthetic agents are not currently used by virtue of being too impractical, dangerous, complex or costly.

Other advantages of the analgesic composition of the present invention may include:

Decreasing the risk of infection and flystrike due to the presence of the barrier.

Reducing pain, which stops the animal from rubbing and biting the wound.

Reducing the need for the use of high doses of insecticides commonly used after animal husbandry procedures, or in some cases completely eliminating the need for insecticides. Thus, insecticide residue levels in the animal may be kept low and the development of insecticide-resistant insects may be discouraged.

The barrier can protect the wound from contact with urine, thus reducing the risk of inflammation and pain.

Yet other advantages of the present invention may be found in the applicants' co-pending PCT application entitled "A Topical Anesthetic Composition", the entire contents of which are hereby incorporated by way of reference.

Throughout this specification, unless in the context of usage an alternative interpretation is required, the term "comprise" (and variants thereof such as "comprising" and "comprised") denotes the inclusion of a stated integer or integers but does not exclude the presence of another integer or other integers.

Any reference to publications cited in this specification is not an admission that the disclosures constitute common general knowledge in Australia or in other countries.

It will be appreciated by one of skill in the art that many changes can be made to the composition and uses exemplified above without departing from the broad ambit and scope of the invention.

We claim:

1. A topical analgesic composition for use on a significant open skin wound, said composition comprising:
    about 40.0 mg/mL to 50.0 mg/mL of lignocaine HCl as a first local anesthetic agent having a rapid onset of action and present in an amount effective to anesthetize the open skin wound;
    0 mg/mL to about 5.0 mg/mL bupivacaine HCl as a second local anesthetic agent having a long duration of action;
    about 36.0 µg/mL to 45.0 µg/mL adrenaline tartrate as a vasoconstrictor present in an amount effective to reduce bleeding from the open skin wound and to decrease the rate of vascular absorption of the local anesthetic agents so as to reduce the risk of systemic toxicity;
    up to about 5.0 mg/mL cetrimide as an antiseptic agent in an amount effective to minimize infection of the open skin wound;
    about 1.5 mg/mL sodium metabisulfite as an antioxidant; and
    about 100 mg/mL non-crystallizing liquid sorbitol (70%) and about 5.0 mg/mL hydroxy cellulose as a carrier applicable to the open skin wound in a fluid form, wherein said carrier:
    adheres to the open skin wound;
    forms a long-lasting viscous barrier over the open skin wound, that is capable of remaining firmly adhered to the open skin wound until the open skin wound has naturally sealed or pain due to the open skin wound has otherwise abated by way of a natural healing process;
    promotes and prolongs contact of the anesthetic agents and the vasoconstrictor with the open skin wound; and
    aids in healing of the open skin wound by minimizing or preventing water loss from the open skin wound and by acting as a barrier against microbial contamination, wherein the composition provides an analgesic effect beyond that attributable to the anesthetic agents alone whilst the barrier covers the skin wound, and wherein said long-lasting viscous barrier is capable of remaining intact over the open skin wound for at least 4 hours and is in a form selected from the group consisting of a gel and spray-solution.

2. The composition of claim 1, wherein said open skin wound is selected from the group consisting of a laceration, a surgical incision, an ulcer, a major abrasion and a major burn.

3. The composition of claim 1, wherein said barrier is in the form of a sticky, viscous gel.

4. The composition of claim 3, wherein said composition is sprayable onto the open wound.

5. The composition of claim 1, wherein said composition comprises one or more ingredients selected from the group consisting of an insecticide, an insect repellent, a skin penetrating enhancer, and a detectable marker for indicating the presence of the composition on the open wound.

6. A topical analgesic composition for use on a significant open skin wound, said composition comprising:
    about 40.0 mg/mL to 50.0 mg/mL lignocaine HCl as a first local anesthetic agent having a rapid onset of action and present in an amount effective to anaesthetize the significant open skin wound;
    up to about 5.0 mg/mL bupivacaine HCl as a second local anesthetic agent having a long duration of action and present in an amount effective to anaesthetize the significant open skin wound;
    about 36.0 µg/mL to 45.0 µg/mL adrenaline tartrate as a vasoconstrictor present in an amount effective to reduce bleeding from the significant open skin wound and to decrease the rate of vascular absorption of the first and second local anesthetic agents so as to reduce the risk of systemic toxicity;
    up to about 5.0 mg/mL cetrimide as an antiseptic agent in an amount effective to minimize infection of the significant open skin wound; and
    a hydrophilic carrier comprising about 100 mg/mL non-crystallizing liquid sorbitol (70%) and about 5.0 mg/mL hydroxy cellulose that:
    adheres to the significant open skin wound;
    forms a long-lasting sticky, viscous, humectant gel barrier over the significant open skin wound that is capable of remaining firmly adhered to the significant open skin wound until the significant open skin wound has naturally sealed or pain due to the significant open skin wound has otherwise abated by way of a natural healing process;
    promotes and prolongs contact of the first and second local anesthetic agents and the vasoconstrictor with the significant open skin wound; and
    aids in healing of the significant open skin wound by minimizing or preventing water loss from the significant open skin wound and by acting as a barrier against microbial contamination, wherein the composition provides an analgesic effect beyond that attributable to the first and second anesthetic agents alone while the barrier covers the significant open skin wound.

7. The composition of claim 6, wherein said hydrophilic carrier is applicable to the significant open skin wound as a sprayable solution.

8. The composition of claim 1, wherein said open skin wound is caused by an animal husbandry procedure.

9. The composition of claim 6, wherein said significant open skin wound is caused by an animal husbandry procedure.

* * * * *